US 7,494,690 B2

United States Patent
Petereit et al.

(10) Patent No.: US 7,494,690 B2
(45) Date of Patent: Feb. 24, 2009

(54) METHOD OF PRODUCING PHARMACEUTICALS OR FOOD SUPPLEMENTS COMPRISING PIGMENTED POLYMER COATINGS

(75) Inventors: Hans-Ulrich Petereit, Darmstadt (DE); Christian Meier, Darmstadt (DE); Erna Roth, Darmstadt (DE)

(73) Assignee: Roehm GmbH & Co. KG, Darmstadt (DE)

(*) Notice: Subject to any disclaimer, the term of this patent is extended or adjusted under 35 U.S.C. 154(b) by 337 days.

(21) Appl. No.: 10/539,808

(22) PCT Filed: Oct. 18, 2003

(86) PCT No.: PCT/EP03/11539

§ 371 (c)(1),
(2), (4) Date: Jun. 20, 2005

(87) PCT Pub. No.: WO2004/058224

PCT Pub. Date: Jul. 15, 2004

(65) Prior Publication Data

US 2006/0078610 A1    Apr. 13, 2006

(30) Foreign Application Priority Data

Dec. 20, 2002   (DE) ............... 102 60 920

(51) Int. Cl.
*B05D 3/00* (2006.01)
*B05D 7/00* (2006.01)
*B32B 5/16* (2006.01)
(52) U.S. Cl. ............. 427/180; 427/185; 427/212; 427/213; 427/352; 428/407
(58) Field of Classification Search ........... 427/180, 427/185, 213, 212, 352; 428/407
See application file for complete search history.

(56) References Cited

U.S. PATENT DOCUMENTS

| 4,433,076 | A |   | 2/1984  | Bauer et al. |
|-----------|---|---|---------|--------------|
| 4,705,695 | A |   | 11/1987 | Lehmann et al. |
| 5,292,522 | A |   | 3/1994  | Petereit et al. |
| 5,711,967 | A | * | 1/1998  | Juch ..................... 424/462 |
| 6,378,789 | B1 | * | 4/2002 | Seaman et al. ........... 239/443 |
| 6,624,210 | B1 |  | 9/2003  | Petereit et al. |
| 6,846,891 | B2 | * | 1/2005 | Petereit et al. ........ 526/303.1 |
| 6,897,205 | B2 | * | 5/2005 | Beckert et al. ........... 514/159 |
| 2003/0064036 | A1 |  | 4/2003 | Petereit et al. |
| 2004/0249035 | A1 |  | 12/2004 | Petereit et al. |
| 2007/0231397 | A1 |  | 10/2007 | Petereit et al. |

FOREIGN PATENT DOCUMENTS

| EP | 0 519 870 | 12/1992 |
|----|-----------|---------|
| EP | 1 240 826 | 9/2002  |
| GB | 1 444 890 | 8/1976  |
| GB | 1 576 075 | 10/1980 |
| WO | 00/05307  | 2/2000  |

OTHER PUBLICATIONS

Abletshauser et al. "Film coating of pellets with insoluble polymers obtained in situ crosslinking in the fluidized bed", Journal of Controlled Release, vol. 27, pp. 149-156, XP009025431 1993.

* cited by examiner

*Primary Examiner*—Rena L. Dye
(74) *Attorney, Agent, or Firm*—Oblon, Spivak, McClelland, Maier & Neustadt, P.C.

(57) ABSTRACT

The invention relates to a method for producing pharmaceuticals or parts thereof or food supplements or parts thereof, by coating substrates with a film-forming coating agent containing a pigment which is incompatible with the coating agent. The invention also relates to appliances for carrying out said method, especially a drum coater, a mushroom mixer, a fluidised bed appliance or a spray sifter comprising multiple spray devices.

10 Claims, No Drawings

METHOD OF PRODUCING PHARMACEUTICALS OR FOOD SUPPLEMENTS COMPRISING PIGMENTED POLYMER COATINGS

The invention relates to a method for producing pharmaceuticals or food supplements comprising pigmented polymer coatings.

PRIOR ART

Abletshauser C. B., describes in "*Film coating of pellets with insoluble polymers obtained in situ crosslinking in fluidized bed*" in *Journal of Controlled Release* 27 (1993), pp. 149-156, a method in which a film-forming polymer, sodium alginate, in aqueous solution and a crosslinker, e.g. a $CaCl_2$ solution or a (meth)acrylate copolymer with tertiary amino group radicals (EUDRAGIT® E), are sprayed simultaneously from two separate spray nozzles onto active ingredient-containing pellets. The film application can take place for example in a fluidized bed apparatus with two spray nozzles installed therein. The method has an approximately equivalent result to sequential application of the two components, but has the advantage of saving time.

WO 00/05307 describes a method for producing a coating agent and binder for oral or dermal pharmaceuticals consisting of (a) 35-98% by weight of a copolymer consisting of free-radical polymerized C1 to C4 esters of acrylic or methacrylic acid and further (meth)acrylate monomers which have functional tertiary ammonium groups, and (b) 1-50% by weight of a plasticizer, and 1-15% by weight of an emulsifier with an HLB of at least 14, where components (a), (b) and (c) are mixed together with or without addition of water and, where appropriate, with addition of an active pharmaceutical ingredient and further conventional additives, and the coating agent and binder is produced by melting, casting, spreading or spraying, where the copolymer (a) is introduced in powder form with an average particle size of 1-40 µm.

Additives which can be incorporated are pigments. Ordinarily, aluminum or iron oxide pigments are dispersed. The usual amounts of pigments employed are between 20 and 60% by weight based on the polymer mixture. However, because of the high pigment-binding capacity, amounts of up to 100% by weight can also be processed.

In a preferred embodiment, the addition of pigments takes place in concentrated form as final layer. Application takes place by spraying as powder or from aqueous suspension with a solids content of 5-30%. The amount required is lower than on incorporation into the polymer layer and is 0.1-2% based on the weight of the pharmaceutical.

PROBLEM AND SOLUTION

WO 00/05307 describes a method for producing a coating agent and binder for oral or dermal pharmaceuticals. Further conventional additives can be added, and the coating agent and binder can be produced by melting, casting, spreading or spraying.

Additives which can are mentioned are inter alia pigments. These can usually be incorporated well using known methodologies. However, it has emerged that in practice problems may arise in spray application on incorporation of pigments which are incompatible with the coating agent. In particular, only a short time after the addition of pigment there may be partial coagulation of the dispersion. As a consequence, the spray nozzles are blocked and the application method must be interrupted.

Since pigments are frequently employed in coating agents, the object was regarded as being to develop the method described in WO 00/05307 further so that spray application is possible reliably and efficiently even with use of pigments as additives.

The object is achieved by a
method for producing pharmaceuticals or parts of pharmaceuticals or food supplements or parts thereof,
by coating substrates with a film-forming coating agent comprising a pigment,
where the film-forming coating agent is a (meth)acrylate copolymer having cationic or anionic groups,
characterized in that
the film-forming coating agent and the pigment are initially present separate from one another as liquid, sprayable, incompatible individual portions in the form of a solution, suspension or dispersion, and
are sprayed simultaneously by spray application by means of one or more spray devices which are capable of separate spraying of liquids, singly or together, and their spray beams overlap,
in such a way that the incompatible individual portions are mixed during the spraying process, impinge on the substrate and form thereon, after evaporation of the liquid, a uniformly pigmented film coating, resulting in the pharmaceutical or the food supplement or the part thereof.

IMPLEMENTATION OF THE INVENTION

The invention relates to a
method for producing pharmaceuticals or parts of pharmaceuticals or food supplements or parts thereof,
by coating substrates with a film-forming coating agent comprising a pigment,
where the film-forming coating agent is a (meth)acrylate copolymer having cationic or anionic groups,
characterized in that
the film-forming coating agent and the pigment are initially present separate from one another as liquid, sprayable, incompatible individual portions in the form of a solution, suspension or dispersion, and
are sprayed simultaneously by spray application by means of one or more spray devices which are capable of separate spraying of liquids, singly or together, and their spray beams overlap,
in such a way that the incompatible individual portions are mixed during the spraying process, impinge on the substrate and form thereon, after evaporation of the liquid, a uniformly pigmented film coating, resulting in the pharmaceutical or the food supplement or the part thereof.

The Film-forming Coating Agent

The film-forming coating agent is a (meth)acrylate copolymer having cationic or anionic groups.

The film-forming coating agent is initially present, separate from the pigment, as liquid, sprayable, incompatible individual portions, preferably in the form of a solution or dispersion.

The film-forming coating agent is a dispersion, e.g. with a solids content of from 10 to 60, preferably 15 to 40, % by weight, comprising a (meth)acrylate copolymer. The dispersion represents a sprayable individual portion which preferably comprises no pigment. Besides the (meth)acrylate copolymer it is possible for pharmaceutically usual excipients such as, for example, plasticizers to be present.

It will be appreciated by the skilled worker that the dispersion may comprise a small proportion of the total amount of pigment to be processed, without an adverse effect on the method of the invention necessarily being associated therewith. This applies in particular when the amount is so small that no incompatibilities occur. Addition of a small, e.g. also soluble, amount of pigment, e.g. less than 0.1-10% by weight based on the polymer, may be worthwhile in individual cases for color identification of the dispersion.

The (meth)acrylate copolymer preferably present in the dispersion is composed of 30 to 80% by weight of free-radical polymerized $C_1$- to $C_4$-alkyl esters of acrylic or methacrylic acid and 70 to 20% by weight of (meth)acrylate monomers having a tertiary amino group in the alkyl radical.

Suitable monomers with functional tertiary amino groups are listed in U.S. Pat. No. 4,705,695, column 3, line 64 to column 4, line 13. Particular mention should be made of dimethylaminoethyl acrylate, 2-dimethylaminopropyl acrylate, dimethylaminopropyl methacrylate, dimethylaminobenzyl acrylate, dimethylaminobenzyl methacrylate, (3-dimethylamino-2,2-dimethyl)propyl acrylate, dimethylamino-2,2-dimethyl)propyl methacrylate, (3-diethylamino-2,2-dimethyl)propyl acrylate and diethylamino-2,2-dimethyl)propyl methacrylate. Dimethylaminoethyl methacrylate is particularly preferred.

The content of monomers with tertiary ammonium groups in the copolymer can advantageously be between 20 and 70% by weight, preferably between 40 and 60% by weight. The proportion of $C_1$- to $C_4$-alkyl esters of acrylic or methacrylic acid is 70-30% by weight. Mention should be made of methyl methacrylate, ethyl methacrylate, butyl methacrylate, methyl acrylate, ethyl acrylate and butyl acrylate.

A suitable (meth)acrylate copolymer with tertiary amino groups may be composed for example of 20-30% by weight of methyl methacrylate, 20-30% by weight of butyl methacrylate and 60-40% by weight of dimethylaminoethyl methacrylate.

A specifically suitable commercially available (meth)acrylate copolymer with tertiary amino groups is composed for example of 25% by weight of methyl methacrylate, 25% by weight of butyl methacrylate and 50% by weight of dimethylaminoethyl methacrylate (EUDRAGIT® E100, EUDRAGIT® E PO).

The copolymers can be obtained in a manner known per se by free-radical bulk, solution, bead or emulsion polymerization. They may before processing be brought to a suitable particle size range by suitable grinding, drying or spraying processes.

Suitable apparatuses for producing powders are familiar to the skilled worker, e.g. air jet mills, pinned disk mills, compartment mills. It is possible where appropriate to include appropriate sieving steps. A suitable mill for industrial large quantities is, for example, an opposed jet mill (Multi No. 4200) which is operated with a gage pressure of about 6 bar.

The average particle size of the powders can be determined as follows:

By air jet sieving to divide up the ground product easily into a few fractions. This method is somewhat less exact than the alternatives in this range of measurement.

A further very suitable measurement method is laser diffraction to determine the particle size distribution. Commercially available apparatuses permit measurement in air (Malvern S3.01 particle sizer) or preferably in liquid media (LOT, Galai CIS 1). A precondition for measurement in liquids is that the polymer does not dissolve therein or the particles change in another way during the measurement. A suitable medium is, for example, a highly dilute (approx. 0.02% strength) aqueous polysorbate 80 solution.

At least 70, preferably 90, % of the particles based on the mass (mass distribution) can preferably be in the 1-40 µm size range.

The average particle diameter must be in the range between 1 and 40, preferably between 5 and 35, in particular between 10 and 20 µm.

The problem of incompatibility also exists with (meth) acrylate copolymers having anionic groups, especially those with comparatively high contents of methacrylic acid residues.

The (meth)acrylate copolymer may consist for example also of 40 to 60% by weight methacrylic acid and 60 to 40% by weight methyl methacrylate or 60 to 40% by weight ethyl acrylate and preferably be in the form of a dispersion (EUDRAGIT® L30D-55 type).

Substrates

The substrates for pharmaceutical applications may be for example active ingredient crystals, active ingredient-containing cores, granules, tablets, pellets or capsules. These may be of regular or irregular shape.

The size of granules, pellets or crystals is between 0.01 and 2.5 mm, that of tablets is between 2.5 and 30.0 mm. Capsules consist for example of gelatin, starch or cellulose derivatives.

The substrates may comprise a biologically active substance (active ingredient) up to 95% and further pharmaceutical excipients up to 99.9% by weight.

Usual production processes are direct compression, compression of dry, moist or sintered granules, extrusion and subsequent rounding off, wet or dry granulation or direct pelleting (e.g. on plates) or by binding of powders (powder layering) onto active ingredient-free beads (nonpareilles) or active ingredient-containing particles.

Besides the active ingredient, further pharmaceutical excipients may be present, such as, for example, binders such as cellulose and derivatives thereof, polyvinylpyrrolidone (PVP), humectants, disintegration promoters, lubricants, disintegrants, (meth)acrylates, starch and derivatives thereof, sugar solubilizers or others.

The substrates usually comprise active pharmaceutical ingredients or food supplements such as, for example, ascorbic acid.

Active Ingredients

Medicinal substances in use can be found in reference works such as, for example, the Rote Liste or the Merck Index.

Biologically Active Substances:

The medicinal substances employed for the purposes of the invention are intended to be used on or in the human or animal body in order, 1. to cure, to alleviate, to prevent or to diagnose disorders, conditions, physical damage or pathological symptoms.
2. to reveal the condition, the status or the functions of the body or mental states.
3. to replace active substances or body fluids produced by the human or animal body.
4. to ward off, to eliminate or to render harmless pathogens, parasites or exogenous substances, or
5. to influence the condition, the status or the functions of the body or mental states.

The formulation of the invention is suitable for administration of in principle any active pharmaceutical ingredients or biologically active substances which can preferably be administered in slow-release form.

These pharmaceutically active substances may belong to one or more active ingredient classes such as ACE inhibitors, adrenergics, adrenocorticosteroids, acne therapeutic agents, aldose reductase inhibitors, aldosterone antagonists, alpha-glucosidase inhibitors, alpha 1 antagonists, remedies for alcohol abuse, amino acids, amebicides, anabolics, analeptics, anesthetic additions, anesthetics (non-inhalational), anesthetics (local), analgesics, androgens, angina therapeutic agents, antagonists, antiallergics, antiallergics such as PDE inhibitors, antiallergics for asthma treatment, further antiallergics (e.g. leukotriene antagonists, antianemics, antiandrogens, antianxiolytics, anti-arthritics, antiarrhythmics, antiatheriosclerotics, antibiotics, anticholinergics, anticonvulsants, antidepressants, antidiabetics, antidiarrheals, anti-diuretics, antidotes, antiemetics, antiepileptics, antifibrinolytics, antiepileptics, antihelmintics, antihistamines, antihypotensives, antihypertensives, antihypertensives, antihypotensives, anticoagulants, antimycotics, antiestrogens, antiestrogens (non-steroidal), antiparkinson agents, antiinflammatory agents, antiproliferative active ingredients, antiprotozoal active ingredients, antirheumatics, antischistosomicides, antispasmolytics, antithrombotics, antitussives, appetite suppressants, arteriosclerosis remedies, bacteriostatics, beta-blockers, beta-receptor blockers, bronchodilators, carbonic anhydrase inhibitors, chemotherapeutic agents, choleretics, cholinergics, cholinergic agonists, cholinesterase inhibitors, agents for the treatment of ulcerative colitis, diuretics, ecto-parasiticides, emetics, enzymes, enzyme inhibitors, enzyme inhibitors, active ingredients to counter vomiting, fibrinolytics, fungistatics, gout remedies, glaucoma therapeutic agents, glucocorticoids, glucocorticosteroids, hemo-statics, cardiac glycosides, histamine H2 antagonists, hormones and their inhibitors, immunotherapeutic agents, cardiotonics, coccidiostats, laxatives, lipid-lowering agents, gastrointestinal therapeutic agents, malaria therapeutic agents, migraine remedies, microbiocides, Crohn's disease, metastasis inhibitors, migraine remedies, mineral preparations, motility-increasing active ingredients, muscle relaxants, neuroleptics, active ingredients for treatment of estrogens, osteoporosis, otologicals, antiparkinson agents, phytopharmaceuticals, proton pump inhibitors, prostaglandins, active ingredients for treating benign prostate hyperblasia, active ingredients for treating pruritus, psoriasis active ingredients, psychoactive drugs, radical scavengers, renin antagonists, thyroid therapeutic agents, active ingredients for treating seborrhea, active ingredients to counter seasickness, spasmolytics, alpha- and beta-sympathomimetics, platelet aggregation inhibitors, tranquilizers, ulcer therapeutic agents, further ulcer therapeutic agents, agents for the treatment of urolithiasis, virustatics, virustatics, vitamins, cytokines, active ingredients for combination therapy with cytostatics, cytostatics.

Examples of suitable active ingredients are acarbose, acetylsalicylic acid, aclarubicin, acyclovir, cisplatin, actinomycin, adenosylmethionine, adrenaline and adrenaline derivatives, alemtuzumab, allopurinol, almotriptan, alosetron, alprostadil, amantadine, ambroxol, amlodipine, amoxicillin, 5-aminosalicylic acid, amitriptyline, amlodipine, amoxicillin, anastrozole, androgen and androgen derivatives, atenolol, atorvastatin, azathioprine, azelaic acid, barbituric acid derivatives, balsalazide, beclomethasone, benzodiazepines, betahistine, bezafibrate, bicalutamide, bimatoprost, budesonide, bufexamac, buprenorphine, bupropion, butizine, calcium antagonists, calcium salts, candesartan, capecitabine, captopril, carbamazepine, caspofungin, cefadroxil, cefalosporins, cefditoren, cefprozil, celetoxib, cetirizine, chenodeoxycholic acid, ciclosporin, cimetidine, clarithromycin, clavulanic acid, clindamycin, clobutinol, clonidine, codeine, caffeine, colestyramine, cromoglicic acid, cotrimoxazole, coumarin and coumarin derivatives, cysteine, cytarabine, cyclophosphamide, cyproterone, cytarabine, dapiprazole, desipramine, desogestrel, desonide, disoproxil, diazepam and diazepam derivatives, dihydralazine, diltiazem, dimenhydrinate, dimethyl sulfoxide, dimeticone, dipyridarnoi, domperidone, and domperidane derivatives, donepzil, dopamine, doxazosin, doxorubizin, doxylamine, diclofenac, divalproex, drospirenone, econazole, emtricitabine, enalapril, ephedrine, epinephrine, epoetin and epoetin derivatives, eprosartan, esomeprazole, estrogen and estrogen derivatives, ethenzamide, ethinestradiol, etofenamate, etofibrate, etofylline, etonorgestrel, etoposide, famciclovir, famotidine, felodipine, fenofibrate, fentanyl, fenticonazole, fexofenadine, fluconazole, fludarabine, flunarizine, fluorouracil, fluoxetine, flurbiprofen, flupirtine, flutamide, fluvastatin, follitropin, formoterol, fosfomicin, frovatriptan, furosemide, fusidic acid, galantamine, gallopamil, ganciclovir, gemfibrozil, gentamicin, progestogen and progestogen derivatives, ginkgo, glibenclamide, glucagon, glucitol and glucitol derivatives, glucosamine and glucosamine derivatives, glycoside antibiotics, urea derivatives as oral antidiabetics, glutathione, glycerol and glycerol derivatives, hypothalamus hormones, goserelin, gyrase inhibitors, guanethidine, gyrase inhibitors, halofantrine, haloperidol, heparin and heparin derivatives, cardiac glycosides, hyaluronic acid, hydralazine, hydrochlorothiazide and hydrochlorothiazide derivatives, hydroxyomeprazole, hydroxyzine, ibuprofen, idarubicin, ifosfamide, imatinib, imipramine, indometacin, indoramine, insulin, interferons, irinotecan, isoconazole, isoprenaline, itraconazole, ivabradines, iodine and iodine derivatives, St. John's wort, potassium salts, ketoconazole, ketoprofen, ketotifen, lacidipine, lansoprazole, letrozol, levodopa, levomethadone, lipoic acid and lipoic acid derivatives, lisinopril, lisuride, lofepramine, lomustine, loperamide, loratadine, magnesium salts, macrolide antibiotics, maprotiline, mebendazole, mebeverine, meclozine, mefenamic acid, mefloquine, meloxicam, mepindolol, meprobamate, meropenem, mesalazine, mesuximide, metamizole, metformin, methadone, methotrexate, methylnaloxone, methylnaltrexones, methylphenidate, methylprednisolone, metixen, metoclopramide, metoprolol, metronidazole, mianserin, miconazole, minocycline, minoxidil, misoprostol, mitomycin, mizolastine, modafinil, moexipril, morphinans, morphine and morphine derivatives, ergot alkaloids, nalbuphine, naloxone, naproxen, narcotine, natamycin, neostigmine, neramexan, nicergoline, nicethamide, nifedipine, niflumic acid, nimodipine, nimorazole, nimustine, nesiritide, nisoldipine, norfloxacin, novamine sulfone, noscapine, nystatin, ofloxacin, olanzapine, olsalazine, omeprazole, omoconazole, ondansetron, orlistat, oseltamivir, oxaceprol, oxacillin, oxiconazole, oxymetazoline, pantoprazole, paracetamol, paroxetine, peginterferon, penciclovir, oral penicillins, pentazocine, pentifylline, pentoxifylline, peptide antibiotics, perindopril, perphenazine, pethidine, plant extracts, phenazone, pheniramine, phenyloin, phenothiazines, phenylbutazone, phenyloin, pimozide, pindolol, piperazine, piracetam, pirenzepine, piribedil, piroxicam, pramipexol, pravastatin, prazosin, procaine, promazine, propiverine, propranolol, propyphenazone, prostaglandins, protionamide, proxyphylline, quetiapine, quinapril, quinaprilate, ramipril, ranitidine, ranolazines, reproterol, reserpine, ribavirin, rifampicin, riluzoles, risedronate, risperidone, ritonavir, ropinirol, rosiglitazone, roxatidine, roxithromycin, ruscogenin, rosuvastatin, rutoside and rutoside derivatives, sabadilla, salbutamol, salicylates, salmeterol, thyroid hormones, scopolamine, selegiline, sertaconazole, sertindole, sertralion, sildenafil, silicates, simvastatin, sitosterol, sotalol, spaglumic acid, sparfloxacin, spectinomycin, spiramycin, spirapril, spironolactone, stavudine, streptomycin, sucralfate, sufentanil, sulbactam, sulfonamides, sulfasalazine, sulpiride, sultamicillin, sultiam, sumatriptan, suxamethonium chloride, tacrine, tacrolimus, tadalafil, taliolol, talsaclidine, tamoxifen, tazarotene, tegaserod, temazepam, teniposide, tenofovir, tenoxicam, terazosin, terbinafine, terbutaline, terfenadine, terlipressin, tertatolol, testosterone and testosterone derivatives, tetracyclines, tetryzoline, theobromine, theophylline, theophylline derivatives, trypsins, thiamazole, thiotepa, tiagabine, tiapride, propionic acid derivatives, ticlopidine, tilidine, timolol, timidazole, tioconazole, tioguanine, tioxolone, tiropramide, tizanidine, tolazoline, tolbutamide, tolcapone, tolnaftate, tolperisone, topiramate, topotecan, torasemide, tramadol, tramazoline, trandolapril, tranylcypromine, trapidil, trazodone, triamcinolone and triamcinolone derivatives, triamterene, trifluperidol, trifluridine, trimetazidines, trimethoprim, trimipramine, tripelennamine, triprolidine, trifosfamide, tromantadine, trometamol, tropalpine, troxerutin, tulobuterol, tyramine, tyrothricin, urapidil, ursodeoxycholic acid, theophylline ursodeoxycholic acid, valaciclovir, valdecoxib, valganciclovir, valproic acid, vancomycin, vardenafil, vecuronium chloride, venlafaxine, verapamil, vidarabine, vigabatrine, viloxazine, vinblastine, vincamine, vincristine, vindesine, vinorelbine, vinpocetine, viquidil, vitamin D and derivatives of vitamin D, warfarin, xantinol nicotinate, xipamide, zafirlukast, zalcitabine, zanamivir, zidovudine, ziprasidone, zoledronic acid, zolmitriptan, zolpidem, zoplicone, zotepine and the like.

The active ingredients can if desired also be used in the form of their pharmaceutically acceptable salts or derivatives, and in the case of chiral active ingredients it is possible to employ both optically active isomers and racemates or mixtures of diastereoisomers. If desired, the compositions of the invention may also comprise two or more active pharmaceutical ingredients.

Pigments

Pigments incompatible with the coating agent are in particular those pigments which, if added directly to the (meth)acrylate copolymer dispersion, e.g. by stirring in, in the amounts normally used of, for example, 20 to 400% by weight based on the dry weight of the (meth)acrylate copolymer, lead to destabilization of the dispersion, coagulation, to signs of inhomogeneity or similarly unwanted effects. The pigments to be used are additionally of course non-toxic and suitable for pharmaceutical purposes and/or for use in food supplements.

Pigments incompatible with the coating agent may be for example alumina pigments. Incompatible pigments are in particular orange yellow S (E110, C.I. 15985, FD&C Yellow 6), indigo carmine (E132, C.I. 73015, FD&C Blue 2), tartrazine (E 102, C.I. 19140, FD&C Yellow 5), Ponceau 4R (E 125, C.I. 16255, FD&C Cochineal Red A), quinoline yellow (E 104, C.I. 47005, FD&C Yellow 10), erythrosine (E127, C.I. 45430, FD&C Red 3), azorubine (E 122, C.I. 14720, FD&C Carmoisine), amaranth (E 123, C.I. 16185, FD&C Red 2), acid brilliant green (E 142, C.I. 44090, FD&C Green S).

The pigment is in the form of a sprayable individual portion, in particular separate from (meth)acrylate copolymer. It is preferred for no (meth)acrylate copolymer to be present. The pigment is preferably suspended alone or together with the release agent in water, e.g. in a concentration of from 5 to 40% by weight, preferably 10 to 30% by weight, based on the total amount. The pigment suspension may additionally comprise pharmaceutically usual excipients such as, for example, plasticizers or dispersion aids, e.g. Mg stearate, talc or precipitated silica (Syloid). It is also possible in principle for the pigment to be dispersed in an organic solvent, e.g. ethanol, acetone or isopropanol. Further excipients may also be present in this case.

It will be appreciated by the skilled worker that the sprayable individual portion comprising the pigment may comprise a small proportion, e.g. 0.1-10% by weight, of the total (meth)acrylate copolymer to be used, without an adverse effect on the method of the invention necessarily being associated therewith.

Spray Device

It is possible to employ or use as spray device those having two or more two-fluid nozzles or one or more three-fluid nozzles.

In a two-fluid nozzle or a three-fluid nozzle, in each case one of the nozzle orifices is supplied with compressed air to atomize the liquid which is sprayed at the same time. The other or the two other spray nozzles serve to eject the respective film-forming coating agent. To carry out the method, therefore, either at least two two-fluid nozzles are required, where one in each case sprays the first film-forming coating agent and the liquid with the further substance, or a three-fluid nozzle, which sprays both simultaneously, is required.

The delivery rates of the sprayed liquids can be influenced independently of one another by the setting of parameters such as, for example, the pump outputs or the spraying pressure and/or the air delivery rates. It is possible in principle for the settings of the spray devices to be carried out manually during the spraying process. In order to obtain reproducible results, it is preferred to control the parameters which influence the delivery rates of the sprayed liquids by means of fixed programs, e.g. by electronic means.

Examples of commercially available spray devices are, for example, the Pilot SIL XII spray gun (double two-fluid nozzle; manufactured by Walther, Wuppertal, Germany), the "Concentric Dual-Feed Nozzle" model (three-fluid nozzle, manufactured by ShinEtsu, Japan) or model 946-S15 (three-fluid nozzle, manufactured by Dusen Schlick GmbH, D-96253 Untersiemau, Germany).

Spray Application

Spray application takes place by means of one or more spray devices which have, singly or together, at least two separate nozzles for liquids and whose spray beams overlap.

The film-forming coating agent and the pigment are initially present separate from one another as sprayable individual portions and are sprayed simultaneously in such as way that the incompatible individual portions are mixed during the spraying, impinge on the substrate and form thereon, after evaporation of the contained liquid, a uniformly pigmented film coating.

The air pressure generating the spray mist is between 0.5 and 3 bar, preferably between 1 and 2 bar. Only in the rare cases where the viscosity of one or both spray liquids is distinctly higher than water may it be necessary to increase the spraying pressure further.

The spraying rate of the two individual components may vary and depends greatly on the batch size, the individual formula and the drying capacity, determined by the air throughput, of the equipment used. Ordinarily, the total of the spraying rates of the two liquids is from 1 to 15 g/kg of cores×min, preferably from 5 to 10 g/kg of cores×min).

The product temperature to be maintained during the spraying depends on the formula of the individual components used and the properties, determined thereby, of the film former. Guideline values are from 15 to 50° C., preferably 20 to 40° C., particularly preferably 25 to 35° C.

Details of the methods, equipment etc. can be found in familiar textbooks, e.g.:

Voigt, R. (1984): Lehrbuch der pharmazeutischen Technologie; Verlag Chemie Weinheim—Beerfield Beach/Florida—Basel.

Sucker, H., Fuchs, P., Speiser, P.: Pharmazeutische Technologie, Georg Thieme Verlag Stuttgart (1991), in particular chapters 15 and 16, pp. 626-642.

Gennaro, A., R. (editor), Remington's Pharmaceutical Sciences, Mack Publishing Co., Easton Pa. (1985), chapter 88, pp. 1567-1573.

List, P. H. (1982): Arzneiformenlehre, Wissenschaftliche Verlagsgesellschaft mbH, Stuttgart.

The film formation takes place through drying preferably during the spray application. The necessary energy input for evaporation of the water can take place through the heated process air, microwaves or other radiation, where appropriate also in vacuo.

The spray application can take place for example in a drum coater, a coating pan, a fluidized bed apparatus or a spray sifter.

The spray application can take place using manually guided spray devices. However, better and more reproducible results are usually obtained with spray devices which are fixed installations, so that these are preferred.

Equipment

The method is particularly preferably carried out with drum coaters, coating pans, fluidized bed apparatuses or spray sifters comprising as spray device one or more three-fluid nozzles, in particular as fixed installation.

Pigmented Pharmaceutical or Food Supplement or Parts Thereof

Pigmented pharmaceuticals or food supplements or parts thereof can be produced or obtained by means of the method of the invention.

In this connection, during the spray application the pigments are entrapped in fractions of seconds in the polymer matrix which results directly through the virtually simultaneous proceeding evaporation of the water. The sprayed individual portions are mixed together in fractions of seconds during the spray application and form, through the virtually simultaneous proceeding evaporation of the water or solvent, a polymer matrix on the surface of the substrates. The resulting molecular matrix structure is therefore novel.

Excipients Customary in Pharmacy

Plasticizers: Substances suitable as plasticizers ordinarily have a molecular weight between 100 and 20 000 and contain one or more hydrophilic groups in the molecule, e.g. hydroxyl, ester or amino groups. Citrates, phthalates, sebacates, castor oil are suitable. Examples of suitable plasticizers are alkyl citrates, propylene glycol, glycerol esters, alkyl phthalates, alkyl sebacates, sucrose esters, sorbitan esters, diethyl sebacate, dibutyl sebacate, fatty acids and esters thereof and polyethylene glycols 4000 to 20 000. Preferred plasticizers are tributyl citrate, triethyl citrate, acetyl triethyl citrate, dibutyl sebacate and diethyl sebacate. The amounts used are between 1 and 35, preferably 2 to 10, % by weight based on the (meth)acrylate copolymer.

Dryers (non-stick agents): Dryers have the following properties: they have large specific surface areas, are chemically inert, are free-flowing and comprise fine particles. Because of these properties, they can advantageously be dispersed homogeneously in melts and reduce the tack of polymers containing highly polar comonomers as functional groups.

Examples of dryers are:

Alumina, magnesium oxide, kaolin, talc, silica (Aerosils), barium sulfate, carbon black and cellulose.

Release Agents (Mold Release Agents)

Examples of release agents are:

esters of fatty acids or fatty amides, aliphatic, long-chain carboxylic acids, fatty alcohols and esters thereof, montan waxes or paraffin waxes and metal soaps; particular mention should be made of glycerol monostearate, stearyl alcohol, glycerol behenic acid ester, cetyl alcohol, palmitic acid, stearic acid, canauba wax, beeswax etc.

Further excipients: Mention should be made here of, for example, stabilizers, colorants, antioxidants, wetting agents, pigments, gloss agents etc. They are used in particular as processing aids and are intended can be to ensure a reliable and reproducible production process and good long-term storage stability. Further excipients customary in pharmacy may be present in amounts of from 0.001% by weight to 30% by weight, preferably 0.1 to 10% by weight, based on the copolymer.

EXAMPLES

EUDRAGIT® E PO is a copolymer of methyl methacrylate, butyl methacrylate, and dimethylaminoethyl methacrylate in the ratio 25:25:50 with an average particle size of 15 µm.

Example 1

A mixture of a spray suspension of a EUDRAGIT® E dispersion formed from 57.0 g of EUDRAGIT® E PO, 4.0 g of sodium lauryl sulfate, 8.55 g of dibutyl sebacate and 278.5 g of water coagulates shortly after stirring in a pigment suspension consisting of 57.0 g of talc, 17.0 g of aluminum pigment orange yellow, 34.0 g of titanium dioxide and 432.0 g of water. Spray application of the mixture is impossible because the spray nozzle becomes blocked.

Example 2

A film-forming dispersion is produced from 57.0 g of EUDRAGIT® E PO, 4.0 g of sodium lauryl sulfate, 8.55 g of dibutyl sebacate and 278.5 g of water by stirring at room temperature. (Polymer dispersion).

A fine-particle suspension is produced from 57.0 g of talc, 17.0 g of aluminum pigment orange yellow, 34.0 g of titanium dioxide and 432.0 g of water at room temperature using a homogenizer (Ultra Turrax) (pigment suspension).

The two liquids are fed by tubing pumps to the nozzle heads of a dual multi-fluid nozzle, e.g. Walther Pilot SIL XII, and atomized so that the mists of the EUDRAGIT® E dispersion and of the pigment suspension are mixed immediately after the nozzle outlet. The coating process is carried out on 3 kg of placebo tablets (diameter 10 mm) in a conventional coating pan (35 cm diameter) while feeding in hot air. The tablet bed temperature is kept at about 30° C. The spraying pressure of both heads was adjusted to about 1 bar. The spraying process lasted about 60 min. Subsequent drying for 15 minutes results in smooth, glossy pigmented films.

Example 3

A mixture of a spray suspension of a EUDRAGIT® E dispersion formed from 114.0 g of EUDRAGIT® E PO, 8.0 g of sodium lauryl sulfate, 17.1 g of dibutyl sebacate and 556.9 g of water coagulates shortly after stirring in a pigment suspension consisting of 34.2 g of magnesium stearate, 17.1 g of cochineal red lake, 28.5 g of titanium dioxide and 319.2 g of water. Spray application of the mixture is impossible because the spray nozzle becomes blocked.

Example 4

A film-forming dispersion is produced from 114.0 g of EUDRAGIT® E PO, 8.0 g of sodium lauryl sulfate, 17.1 g of dibutyl sebacate and 556.9 g of water by stirring at room temperature. (Polymer dispersion). A fine-particle suspension is produced from 24.2 g of magnesium stearate, 17.1 g of cochineal red lake, 28.5 g of titanium dioxide and 319.2 g of water at room temperature using a homogenizer (Ultra Turrax) (pigment suspension).

The two liquids are fed by tubing pumps to the nozzle heads of a dual multi-fluid nozzle, e.g. Walther Pilot SIL XII, and atomized so that the mists of the EUDRAGIT® E dispersion and of the pigment suspension are mixed individually after the nozzle outlet. The coating process is carried out on 3 kg of placebo tablets (diameter 10 mm) in a conventional coating pan (35 cm diameter) while feeding in hot air. The tablet bed temperature is kept at about 30° C. The spraying pressure of both heads was adjusted to about 1 bar. The spraying process lasted about 74 min. Subsequent drying for 15 minutes results in smooth, glossy pigmented films.

The invention claimed is:

1. A method for producing pharmaceuticals or parts of pharmaceuticals or food supplements or parts thereof, comprising:
    preparing a sprayable solution, suspension or dispersion of a film-forming coating agent in a liquid;
    preparing a separate sprayable solution, suspension or dispersion of a pigment in a liquid;
    simultaneously spraying by spray application onto a substrate of the pharmaceuticals or parts of pharmaceuticals or food supplements or parts thereof with the solution, suspension or dispersion of a film-forming coating agent and the solution, suspension or dispersion of a pigment;
    thereby coating the substrate with the film-forming coating agent comprising the pigment;
    evaporating the liquid of each solution, suspension or dispersion;
    forming a uniformly pigmented film coating on the pharmaceuticals or parts of pharmaceuticals or food supplements or parts thereof;
    wherein the film-forming coating agent is a (meth)acrylate copolymer having cationic or anionic groups,
    the sprayable solution, suspension or dispersion of a film-forming coating agent and the sprayable solution, suspension or dispersion of a pigment are incompatible with respect to destabilization of the dispersion, coagulation, signs of inhomogeneity or similarly unwanted effects if combined before spraying, and
    the simultaneously spraying by spray application comprises one or more spray devices which separately spray liquids, singly or together, and separate spray beams of the one or more spray devices overlap.

2. The method according to claim 1, wherein the (meth)acrylate copolymer consists of 30 to 80% by weight free-radical polymerized $C_1$ to $C_4$ alkyl esters of acrylic or methacrylic acid and 70 to 20% by weight (meth)acrylate monomers having a tertiary amino group in the alkyl radical.

3. The method according to claim 1, wherein the (meth)acrylate copolymer consists of 40 to 60% by weight methacrylic acid and 60 to 40% by weight methyl methacrylate or 60 to 40% by weight ethyl acrylate.

4. The method according to claim 1, wherein the substrates are selected from the group consisting of active ingredient crystals, active ingredient-containing cores, tablets, granules, pellets and capsules.

5. The method according to claim 1, wherein the pigment incompatible with the coating agent is an aluminum pigment.

6. The method according to claim 1, wherein the pigment incompatible with the coating agent is selected from the group consisting of orange yellow S (E110, C.I. 15985, FD&C Yellow 6), indigo carmine (E132, C.I. 73015, FD&C Blue 2), tartrazine (E 102, C.I. 19140, FD&C Yellow 5), Ponceau 4R (E 125, C.I. 16255, FD&C Cochineal Red A), quinoline yellow (E 104, C.I. 47005, FD&C Yellow 10), eythrosine (E127, C.I. 45430, FD&C Red 3), azorubine (E 122, C.I. 14720, FD&C Carmoisine), amaranth (E 123, C.I. 16185, FD&C Red 2), and acid brilliant green (E 142, C.I. 44090, FD&C Green S).

7. The method according to claim 1, wherein the one or more spray devices comprises two or more two-fluid nozzles or one or more three-fluid nozzles.

8. The method according to claim 1, wherein the spray application takes place in a drum coater, a coating pan, a fluidized bed apparatus or a spray sifter.

9. The method according to claim 8, wherein the spray application takes place by spray devices as fixed installation.

10. The method for producing pharmaceuticals or parts of pharmaceuticals or food supplements or parts thereof, according to claim 1, further comprising applying a sealing layer to the substrate of the pharmaceuticals or parts of pharmaceuticals or food supplements or parts thereof before the simultaneously spraying by spray application onto the substrate of the pharmaceuticals or parts of pharmaceuticals or food supplements or parts thereof with the solution.

* * * * *